United States Patent
Kim et al.

(10) Patent No.: US 7,020,542 B2
(45) Date of Patent: Mar. 28, 2006

(54) APPARATUS FOR MEASURING AND FIXING THE THREE-DIMENSIONAL LOCATION OF MEDICAL INSTRUMENT

(75) Inventors: Mun Sang Kim, Seoul (KR); Sung Kee Park, Seoul (KR); Jong Suk Choi, Seoul (KR); Chang Hyun Cho, Seoul (KR); Dong Seok Ryu, Seoul (KR); Yo Ha Hwang, Seoul (KR); Min Joo Choi, Jeju-do (KR)

(73) Assignee: Korea Institute of Science and Technology, Seoul (KR)

( * ) Notice: Subject to any disclaimer, the term of this patent is extended or adjusted under 35 U.S.C. 154(b) by 294 days.

(21) Appl. No.: 10/437,625

(22) Filed: May 14, 2003

(65) Prior Publication Data
US 2003/0216821 A1 Nov. 20, 2003

(30) Foreign Application Priority Data
May 14, 2002 (KR) ............. 10-2002-0026357

(51) Int. Cl.
*G06F 19/00* (2006.01)

(52) U.S. Cl. ............. 700/245; 700/131; 700/250; 700/251; 700/257; 700/258; 700/259; 700/260; 318/568.11; 318/568.13; 318/568.16; 318/568.2; 901/1; 701/10; 701/23; 701/26

(58) Field of Classification Search ............. 701/10, 701/23, 26; 700/245, 250, 251, 131, 13, 700/257–262; 600/101–102, 109, 118, 426, 600/429, 595; 606/1, 130–132; 318/568.11, 318/568.13, 568.16, 568.2; 348/165; 901/1
See application file for complete search history.

(56) References Cited

U.S. PATENT DOCUMENTS

| | | | |
|---|---|---|---|
| 6,594,552 B1 * | 7/2003 | Nowlin et al. | 700/260 |
| 6,684,129 B1 * | 1/2004 | Salisbury, Jr. et al. | 700/245 |
| 6,839,612 B1 * | 1/2005 | Sanchez et al. | 700/245 |
| 2003/0060927 A1 * | 3/2003 | Gerbi et al. | |
| 2003/0109957 A1 * | 6/2003 | Sanchez et al. | 700/245 |
| 2003/0114962 A1 * | 6/2003 | Niemeyer | 700/245 |
| 2003/0220541 A1 * | 11/2003 | Salisbury et al. | 600/101 |

OTHER PUBLICATIONS

Papp et al., Intelligent medical instruments, 1988, IEEE, p. 18-23.*

Twomey et al., an instrumetn for measuring the absolute output accoustic intensity, effective radiating are adn beam non-unformity ratio of medical ultrosound devices, 1989, IEEE, p. 1455-1456.*

* cited by examiner

Primary Examiner—Thomas G. Black
Assistant Examiner—McDieunel Marc
(74) Attorney, Agent, or Firm—Harness, Dickey & Pierce, P.L.C.

(57) ABSTRACT

An apparatus for measuring and fixing the three-dimensional location of medical instrument that can be easily placed at a desired location by a user. In addition, a medical apparatus for measuring the three-dimensional locations of an apparatus fixed at an end portion of a cancer and an external apparatus and fixing the apparatus at an end portion of the cancer, which can be easily placed at a desired location by a user and carries out the location-fixing and measuring at the same time. The apparatus is applicable for various medical fields such as the measurement of the location and orientation of an external apparatus, the measurement of relative locations of a medical instrument contacted to an end-portion of a cancer and the object body, and the fixation of the instrument at a desired location.

13 Claims, 8 Drawing Sheets

APPARATUS FOR MEASURING AND FIXING THE THREE-DIMENSIONAL LOCATION OF MEDICAL INSTRUMENT

BACKGROUND OF THE INVENTION

1. Field of the Invention

The present invention relates to an apparatus for measuring and fixing the three-dimensional location of medical instrument, and more particularly to an apparatus for measuring and fixing the three-dimensional location of medical instrument simultaneously, which can be easily placed at a desired location by a user.

2. Description of the Related Art

In a medical operation like a calculus elimination using shock-wave, it is generally required to locate an ultrasonic prove, used for monitoring the calculus-crashing process, etc., precisely at the focus of the shock-wave. And, it is also generally required to know the three-dimensional coordinates and orientation of the instrument. This requires a function to locate a medical instrument and an external device precisely at a certain location as well as to fix the instrument thereto.

A robot, constituted of driving joints like electric motors, is able to measure and fix the three-dimensional location, however, it is mostly used as a fixing apparatus. And a direct enlightening method is widely being used for a robot to be used as a measuring apparatus, however, the constitution and/or the control is difficult.

In addition, a haptic apparatus has similar functions. Its basic structure is identical to a general robot, however, it is designed to reflect virtual circumstances and/or a remote robotic power, and thus its usage as a three-dimensional measuring apparatus is identical to that of an industrial robot. In this apparatus, a master device for remote control and a laser measurement technique are only applicable for measuring the location. Thus, without an extra fixing tool, it has difficulties in being fixed at a desired location.

SUMMARY OF THE INVENTION

The present invention is proposed to solve the problems of the prior art mentioned above. It is therefore the object of the present invention to provide a medical apparatus for measuring the three-dimensional locations of an apparatus fixed at an end portion of a cancer and an apparatus located at the exterior of the cancer and fixing the apparatus fixed at an end portion of the cancer thereto, which can be easily placed at a desired location by a user and carries out the location-fixing and measuring at the same time.

To achieve the object mentioned above, the present invention provides an apparatus for measuring and fixing the three-dimensional location of medical instrument, which can be easily placed at a desired location by a user and carry out measuring and fixing the location simultaneously, comprising:

a link device, having multi-degrees-of-freedom with comprising numbers of rotational joints, interlocked with PC, an external controller, and able to communicate through a CAN (control area network) bus;

a balancing means, of which a weight and a spring is installed at each joint, for compensating the movement and self-weight of the link device for a user to move the link device easily;

a module means for modularizing the location-detection means and fixing means including the controllers applied to the joints for easy assembly, repair and replacement;

a dispersed control system comprising a main controller and dispersed controllers installed at the joints for carrying out instrumental calculation by packet transmission through CAN bus with PC, an external controller;

an electric breaking means, controlled to be operated by an external switch or program, for enabling the link device to be freely moved and fixing the location of the link device; and at least two or more fixing pins constituted at the end-section of the link device and a pin-hole means at the base of the link device, where the fixing pins can be assembled, for enlightening the origin of the link device, characterized in that the apparatus is able to enlighten the origin of the link device and measure the relative coordinates of the link device and an external device by fabricating a pin-hole means, possibly being assembled with the fixing pins constituted at the end-section of the link device, at the external device.

Figure 1:
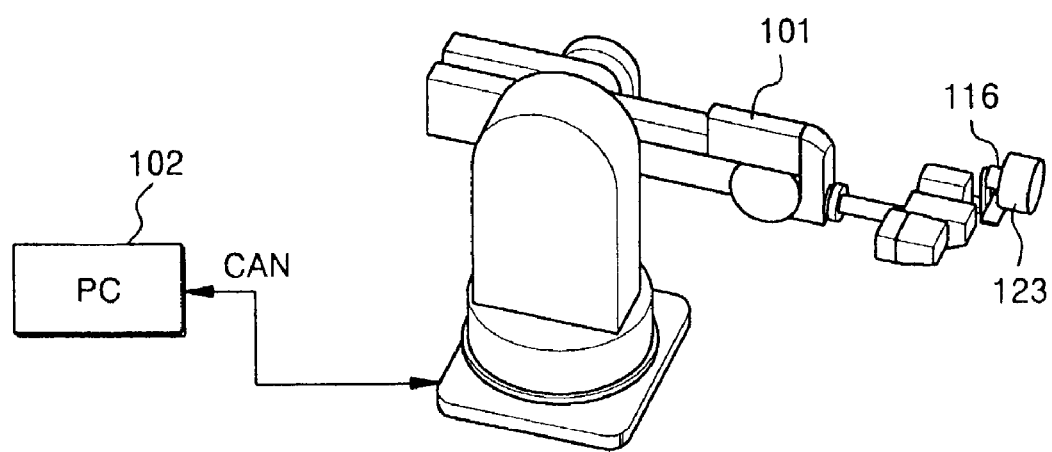
FIG. 1 is a view illustrating the overall structure of an apparatus for measuring and fixing the three-dimensional location of medical instrument in accordance with the present invention.

DESCRIPTION OF THE NUMERALS ON THE MAIN PARTS OF THE DRAWINGS 1, 2, 3, 4, 5 and 6: joints
101: a 6-degrees-of-freedom link device
102: a PC
103, 104: balancing weights
105: a balancing spring
106: an electric break
107: an encoder
108: a dispersed controller
109: an output shaft
110, 111: pulleys
112: a frame
113: an electric break amplifier
114: a break switch
115: a break relay
116: a tool installing section 117, 118: pins
119: a block
120, 121: pin-holes
122: an external apparatus
123: a medical instrument

DETAILED DESCRIPTION OF THE EMBODIMENTS

Hereinafter, referring to appended drawings, the structures and operation principles of embodiments of the present invention are described in detail.

FIG. 1 is a view illustrating the overall structure of an apparatus for measuring and fixing the three-dimensional location of medical instrument in accordance with the present invention. Referring to FIG. 1, the apparatus comprises a 6-degrees-of-freedom (DOF) link device (101), a PC (102) and a tool installing section (116). A medical instrument (123) like an ultrasonic probe is installed at the tool installing section (116). The PC (102) communicates with 6 encoder interface boards installed at the 6-DOF link device (101) through a CAN (Control Area Network) bus. Here, instead of the 6-DOF link device (101), a link device for a limited motion having the function of a spatial-spherical movement can be used.

Figure 2:
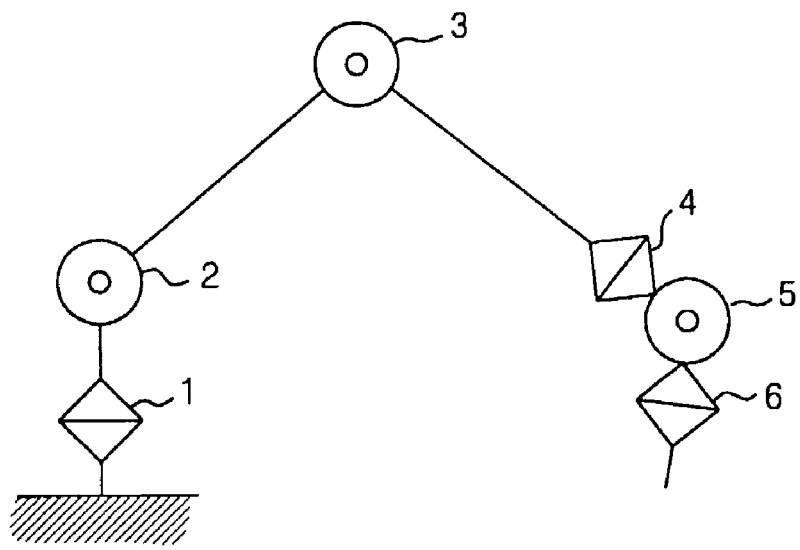
FIG. 2 is a view illustrating the overall structure of a 6-degrees-of-freedom link device described in FIG. 1.

FIG. 2 is a view illustrating the overall structure of a 6-DOF link device, which comprises 6 rotational joints (1, 2, 3, 4, 5 and 6), like a general industrial robot, for indicating all the spatial locations and directions.

For using the system of the present invention as a location measurement apparatus, it is the most preferable operation method that a user grips an end of the link device and moves it into a desired location.

Figure 3:
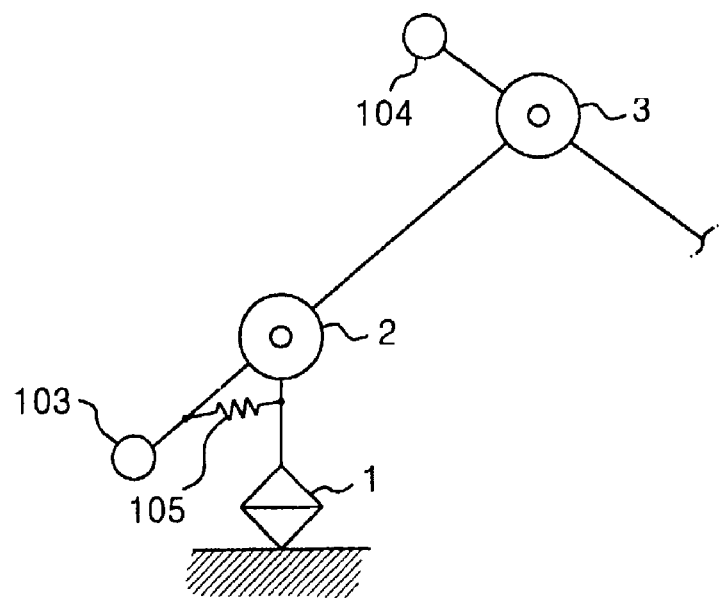
FIG. 3 is a view illustrating the structure of a joint, with a balancing weight and spring being installed thereat, described in FIG. 2.

For compensating the self-weight of the link device and assisting a user to easily move the 6-DOF link device, balancing weights (103, 104) and a balancing spring (105) are installed at the joints (2, 3) as described in FIG. 3.

Figure 4:
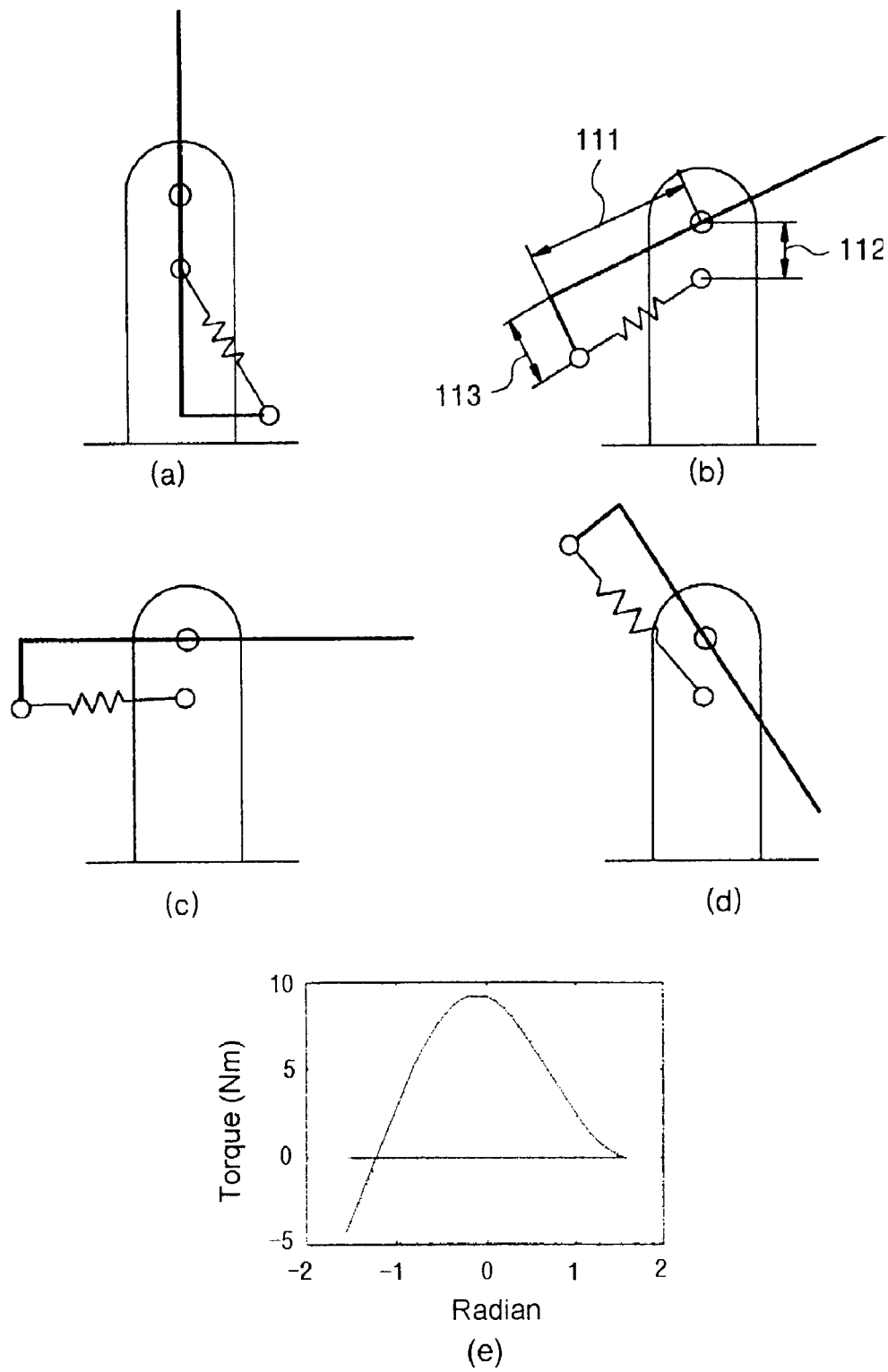
FIGS. 4(a)~4(e) are views illustrating the operating principle and the function of a balancing spring.

In FIGS. 4(a)~4(d), the operation principle of a balancing spring (105) is described, and the output torque of the joint (2) generated by the balancing spring (105) is described in FIG. 4(e).

When the device is being operated in turns of FIGS. 4(a)–4(b)–4(c)–4(d), the torque applied to the joint (2) by the balancing spring (105) is described in FIG. 4(e) along with the rotation angle of the joint (2). The shape described in FIG. 4(c) represents the origin of the joint (2), FIG. 4(d) shows the shifts of the joint (2) to the positive and negative directions, and FIGS. 4(a) and 4(b) show the shift to the positive direction.

In the case of the origin of the joint (2), described in FIG. 4(c), the maximum moment is being occurred due to self-weight. Looking into the graph of output torque described in FIG. 4(e), it can be noticed that the balance torque generated by the balancing spring (105) has its maximum value around the origin, and thus it is confirmed that the balancing spring (105) is installed appropriately.

The balancing weight (104) described in FIG. 3 is constituted of the sensor and break bundle installed at the joint (4) without constituting an extra weight. Similarly, the balancing weight (103) is constituted of the sensor and break bundle installed at the joint (3) and an additional weight to minimized the constituent weight. Here, in the case of a light link device, either a balancing weight (104) or a balancing spring (105) is being used alone. And in the case of a heavy link device, a balancing weight (104) and a balancing spring (105) are being used together.

Figure 5:
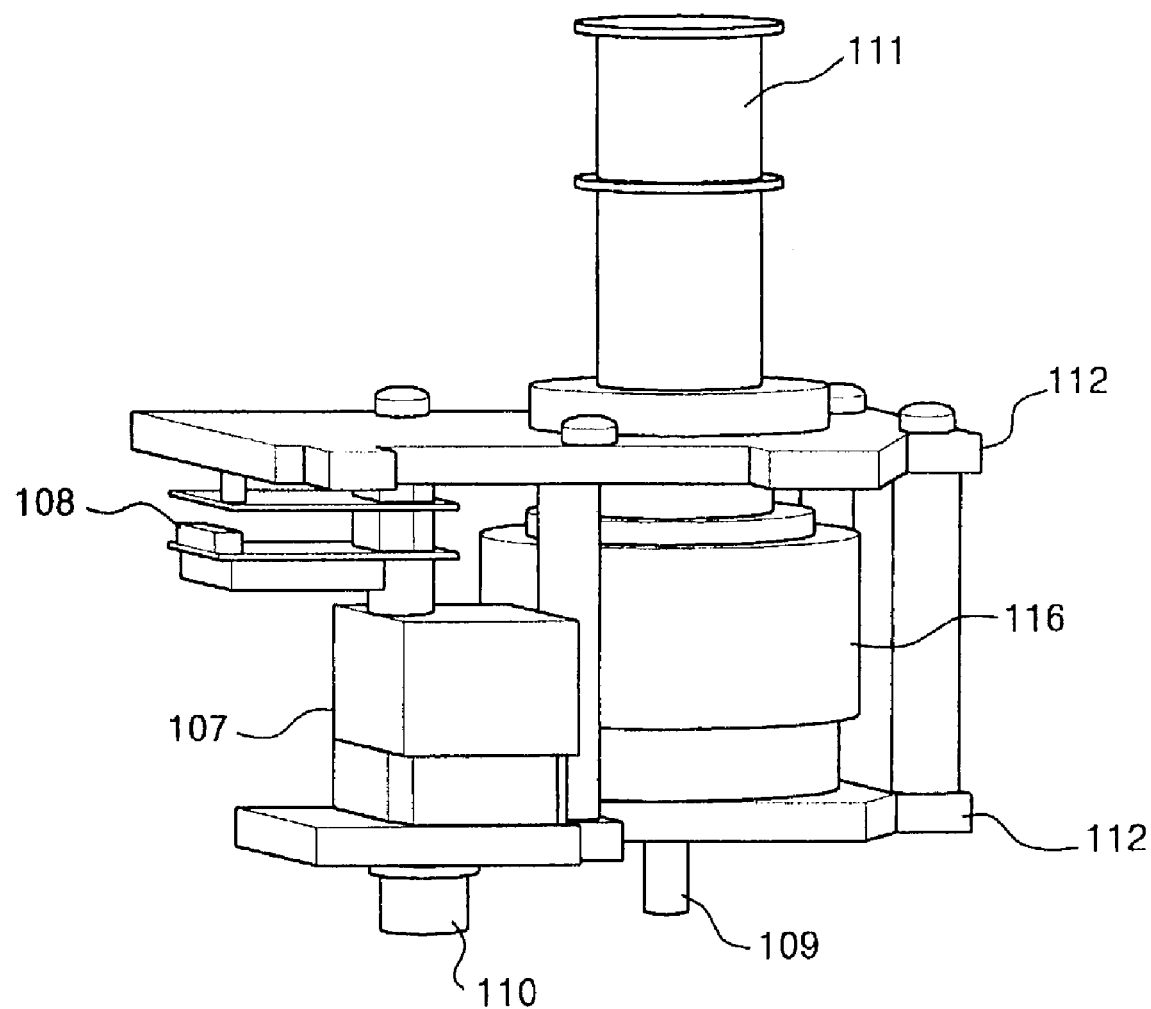
FIG. 5 is a view illustrating a break module installed at the joint described in FIG. 2.

FIG. 5 shows the structure of a break module installed at the joint (2) described in FIG. 3, and the structures are the same at all the joints. This kind of modularized structure can minimize the assembling errors of the parts and has advantage that the repair and replacement of the parts are comparatively easy.

As described in FIG. 5, an electric break (106), an encoder (107) and a dispersed controller (108) are installed at the frame (112) of each joint. They are installed at joint (2) and joint (3) respectively as a module as described in FIG. 5. Considering the spatial efficiency, they are separately installed at joints (1, 4, 5 and 6). A break, instead of an electric motor, is installed at each joint, and thus a user can easily move the 6-DOF link device (101).

Here, in addition to the sensor for detecting the location, an additional sensor for detecting the temperature can also be constituted into a module.

The numeral 109 in FIG. 5 indicates the output shaft of an electric break (106), and a pulley (111) is installed at the output shaft (109) to be connected to the joint (2) by a timing belt. To increase the locative resolution, an accelerating section using a timing belt is installed between the encoder (107) and the output shaft (109).

Figure 6:
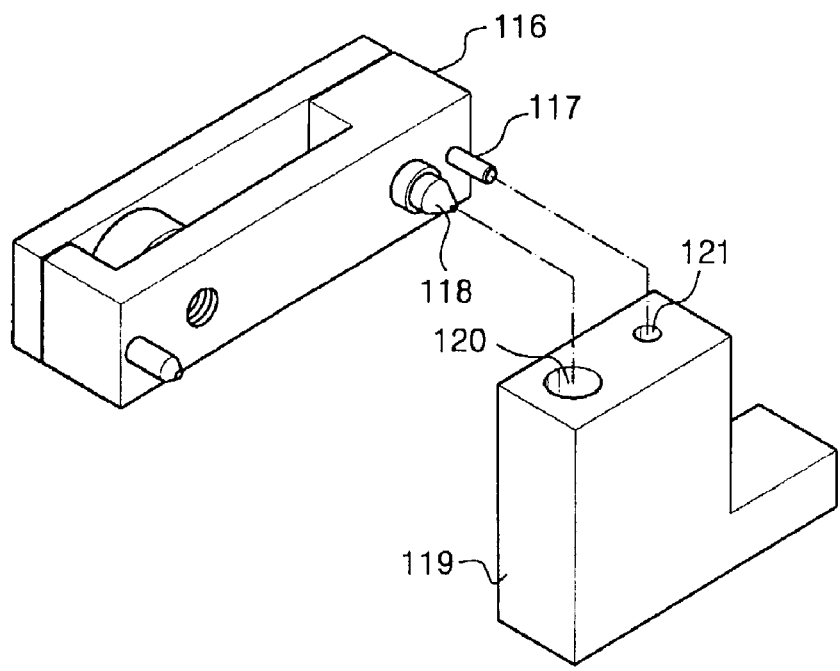
FIG. 6 is a view illustrating a jig for enlightening the origin of the 6-degrees-of-freedom link device described in FIG. 1.

FIG. 6 is a view illustrating a jig for enlightening the origin of the 6-DOF link device (101). A tool installing section (116) is connected to the shaft of the joint (6), and pins (117, 118) are installed thereat. A pin (118) is installed on the shaft of the joint (6) and a pin (117) is eccentrically installed at the shaft of the joint (6).

The pin (118) is installed for fixing the end of the link device, i.e. the location of the tool installing section (116), and the pin (117) is for fixing the orientation. A block (119) is installed at the fixing section of the 6-DOF link device (101) and pin-holes (120, 121), where the pins (117, 118) are being inserted, are fabricated thereon. Once the pins (117, 118) are inserted into the corresponding pin-holes (120, 121), the end of the 6-DOF link device (101) is fixed, and thereby the accurate origin can be set.

Here, the pins (117, 118) can have the shape of a cylinder, a tapered cylinder, a rectangle, or the like.

The origin enlightening method using the pins (117, 118) described above can be substituted with the methods of using a hall sensor or an absolute-angle measuring encoder used in an industrial robot, however, they cost more and require an additional circuit.

Figure 7:
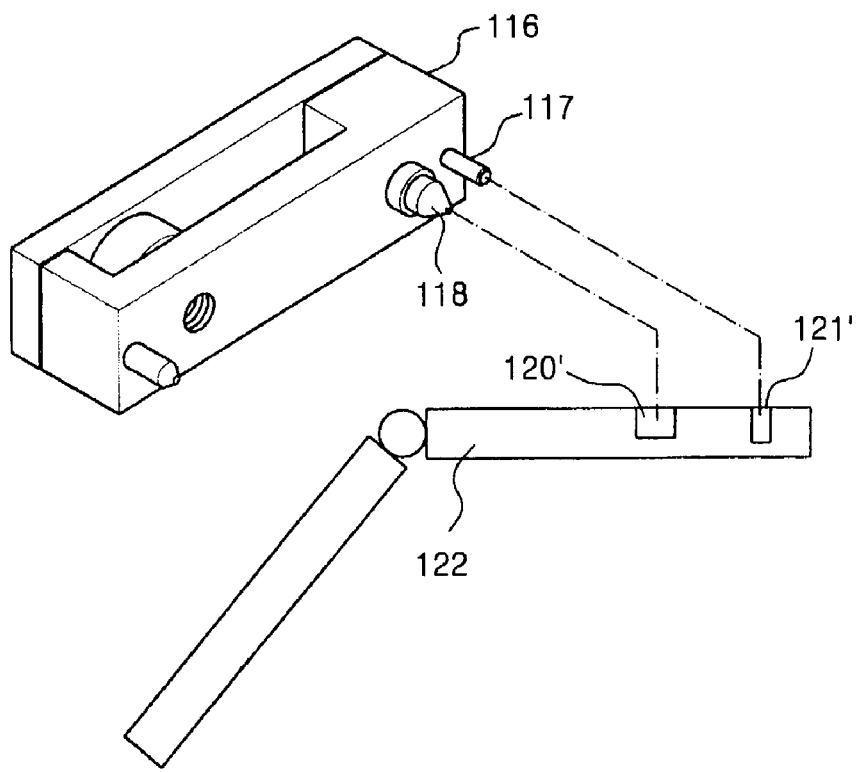
FIG. 7 is a view illustrating the method for measuring the location of an arbitrary external apparatus.

As described in FIG. 7, when a user intends to know the location and the orientation of an arbitrary external apparatus (122), he (or she) can fabricate pin-holes (120', 121'), corresponding to the pins (117, 118), at the apparatus (122), insert the tool installing section (116) into the apparatus (122), read the encoder value at the time, and calculate the instrumental equation.

Here, the external apparatus (122) can be a general apparatus such as a table or an X-ray apparatus, and the installing location can be selected anywhere as far as it can be assembled to the end of the link device.

Figure 8:
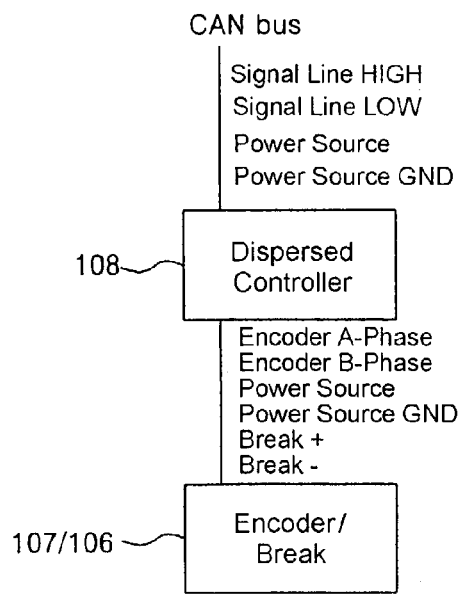
FIG. 8 is a view illustrating the interfacing relation between a dispersed controller and an encoder/break described in FIG. 5.

FIG. 8 is a view illustrating the interfacing relation between a dispersed controller (108) and an encoder/break (107/106) described in FIG. 5. A dispersed controller (108) is connected to the corresponding encoder/break (107/106) by a signal line and an electric power line, and it is connected to other dispersed controllers (108) or an external controller, PC (102), through CAN bus.

Figure 9:
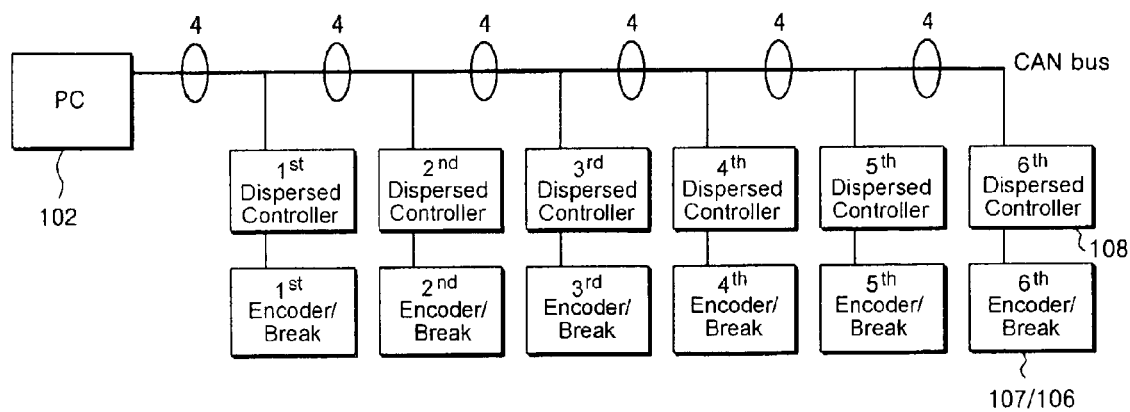
FIG. 9 is a view illustrating the overall structure of a dispersed control system.

FIG. 9 is a view illustrating the overall structure of a dispersed control system, and it is shown that each dispersed controller (108) corresponding to each joint and the break modules comprising the encoder/break (107/106) are connected to each other by the electric power line and CAN bus signal line.

Here, either wired- or wireless-type communication system such as a CAN bus, an USB (universal serial bus), a ProfiBus, or a BlueTooth is applicable for the dispersed control system.

A PC, a micro-controller or a special CPU having the function of digital signal processing (DSP) can be used as a main controller, and a micro-controller or a special CPU having the function of DSP can be used as a dispersed controller (108).

In general, a dispersed controller (108) takes charge of interfacing the sensor only, and all the calculations are being carried out by the main controller. However, some calculations can be carried out by the dispersed controller (108), having the function of data conversion and signal processing, and the other calculations can be carried out by the main controller.

A PC (102), an external controller, reads the values of the encoders by packet transmission with the dispersed controllers (108) through CAN bus and carries out the instrumental calculation. This kind of dispersed control system can remarkably reduce the number of electric wiring, and in the software-side viewpoint, it partially allocates some portion of the calculations, to be calculated by PC (102), to the dispersed controllers (108), and thereby makes it possible that the PC (102) can perform other useful functions such as an ultrasonic image processing and a network communication.

Figure 10:
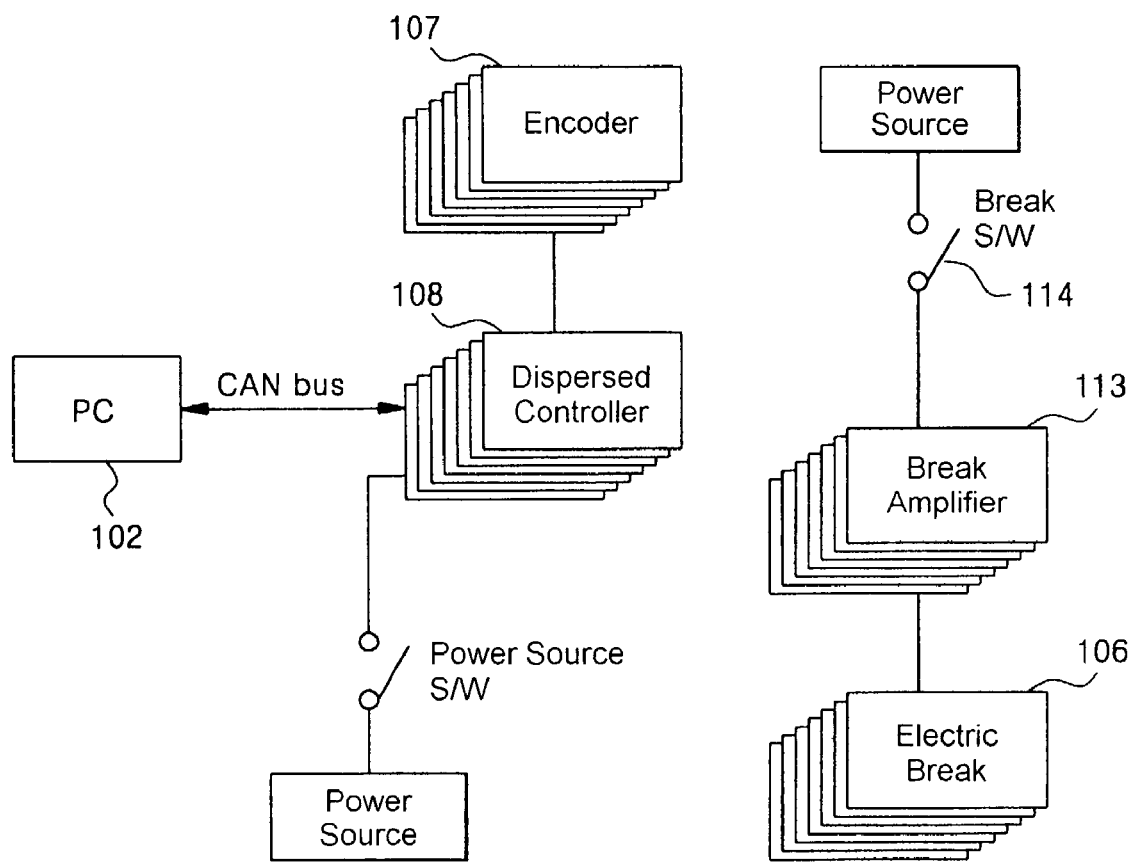
FIG. 10 is a view illustrating a break control system using an external switch.

FIG. 10 is a view illustrating a break control system using an external switch. The control on the electric break (106) can be achieved by simply applying the electric power to the electric break amplifier (113) or applying a signal to the enable port of the electric break amplifier (113) through the break switch (114).

Here, the external switch can be installed at the end or the base of the link device, or it can also be constituted to be independent of the link device by using an extra cable. In addition, the control on the electric break (106) can be carried out by either an independent control mechanism, in which an external switch is connected to the enable port of the break amplifier or the electric power is directly connected to the break amplifier, or a control mechanism controlling the switch signal using a main controller and dispersed controllers.

The self-control of the electric break can be carried out in a way that the break is released with power being applied and tightened with power being cut or vice versa. As a break having the similar functions to an electric break, a solenoid, a hydraulic break using a speed control valve, a break using magneto-hydraulic fluids, or a break using electro-hydraulic fluids can be used.

Figure 11:
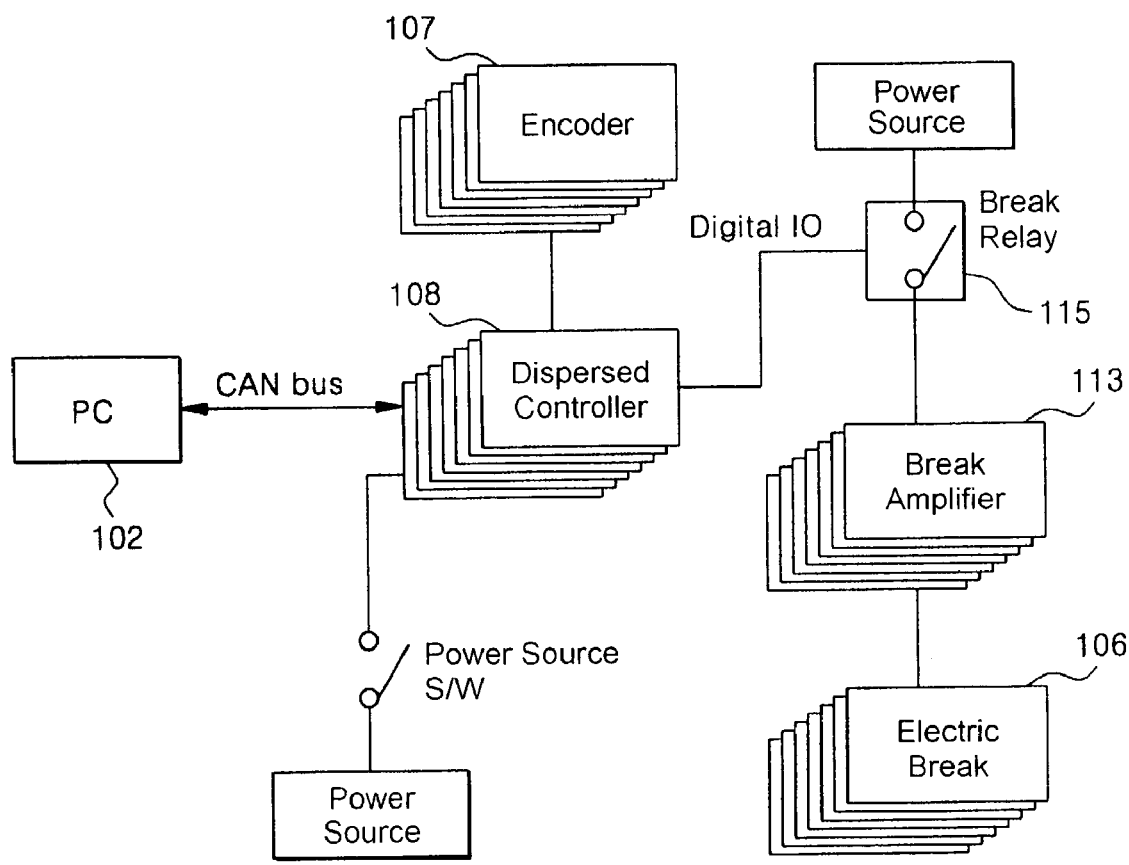
FIG. 11 is a view illustrating a break control system using digital input/output signals.

FIG. 11 shows a break control system, in which digital input/output signals of a dispersed controller (108) is connected to the break relay (115), for controlling the electric break (106) by software instead of using a break switch (114), as illustrated in FIG. 10. The electric break (106) is controlled to be released when the device is being moved and tightened when the device is being fixed.

As mentioned thereinbefore, an apparatus for measuring and fixing the three-dimensional location of medical instrument in accordance with the present invention is applicable for various medical fields such as the measurement and the calibration of the location and the orientation of an external apparatus, the measurement of relative locations of a medical instrument contacted to an end-portion of a cancer and the object body, and the fixation of the instrument at a desired location.

Since those having ordinary knowledge and skill in the art of the present invention will recognize additional modifications and applications within the scope thereof, the present invention is not limited to the embodiments and drawings described above.

The entire content of Priority Document 2002-26357 is incorporated herein by reference.

What is claimed is:

1. An apparatus for measuring and fixing a three-dimensional location of medical instrument, which can be easily placed at a desired location by a user and carry out measuring and fixing the location simultaneously, comprising:
   a link device, having multi-degrees-of-freedom with comprising numbers of rotational joints, interlocked with PC, an external controller, and able to communicate through a CAN (control area network) bus;
   a balancing means, of which a weight and a spring is installed at each joint, for compensating the movement and self-weight of said link device for a user to actuate the link device easily;
   a module means for modularizing location-detection means and fixing means including controllers applied to said joints for easy assembly, repair and replacement;
   a dispersed control system comprising a main controller and dispersed controllers installed at said joints for instrumental calculation by packet transmission through said CAN bus with said PC, an external controller;
   an electric breaking means, controlled to be operated by an external switch or program, for enabling said link device to be moved freely and fixing the location of said link device; and
   at least two or more fixing pins constituted at the end-section of said link device and a pin-hole means at the base of said link device, where the fixing pins can be assembled, for enlightening the origin of said link device, characterized in that said apparatus is able to enlighten the origin of said link device and measure the relative coordinates of said link device and an external device by fabricating a pin-hole means, possibly being assembled with said fixing pins constituted at the end-section of said link device, at said external device.

2. An apparatus for measuring and fixing the three-dimensional location of medical instrument as claimed in claim 1, characterized in that said link device having multi-degrees-of-freedom has 6-degrees-of-freedom or containing a link device for a limited motion having the function or a spatial-spherical movement.

3. An apparatus for measuring and fixing the three-dimensional location of medical instrument as claimed in claim 1, characterized in that said balancing means uses either a balancing weight or a balancing spring alone in the case of a light link device, and in the case of a heavy link device, it can use a balancing weight and a balancing spring together.

4. An apparatus for measuring and fixing the three-dimensional location of medical instrument as claimed in claim 1, characterized in that said module means further comprises a location detection sensor and an additional device having the function of temperature sensing.

5. An apparatus for measuring and fixing the three-dimensional location of medical instrument as claimed in claim 1, characterized in that either wired- or wireless-type communication system such as a CAN bus, an USB (universal serial bus), a ProfiBus, or a BlueTooth is applied to said dispersed control system.

6. An apparatus for measuring and fixing the three-dimensional location of medical instrument as claimed in claim 1 or 5, characterized in that said dispersed control system uses a PC, a micro-controller or a special CPU having the function of digital signal processing (DSP) as a main controller and a micro-controller or a special CPU having the function of DSP as a dispersed controller.

7. An apparatus for measuring and fixing the three-dimensional location of medical instrument as claimed in claim 6, characterized in that said dispersed controllers take charge of interfacing the sensor only and all the calculations are being carried out by said main controller, or some calculations are carried out by said dispersed controllers having the function of data conversion and signal processing and the other calculations are carried out by said main controller.

8. An apparatus for measuring and fixing the three-dimensional location of medical instrument as claimed in claim 1, characterized in that said external switch of said electric breaking means is installed at the end or the base of said link device or constituted to be independent of said link device by using an extra cable.

9. An apparatus for measuring and fixing the three-dimensional location of medical instrument as claimed in claim 1 or 8, characterized in that the control on said electric breaking means is carried out by either an independent control mechanism, in which said external switch is connected to the enable port of the break amplifier or the electric power is directly connected to the break amplifier, or a control mechanism controlling the switch signal using a main controller and dispersed controllers.

10. An apparatus for measuring and fixing the three-dimensional location of medical instrument as claimed in claim 9, characterized in that the self-control of said electric breaking means can be carried out in a way that the break is released with power being applied and tightened with power being cut or vice versa.

11. An apparatus for measuring and fixing the three-dimensional location of medical instrument as claimed in claim 9, characterized in that a solenoid, a hydraulic break using a speed control valve, a break using magneto-hydraulic fluids or a break using electro-hydraulic fluids can be used as said electric breaking means.

12. An apparatus for measuring and fixing the three-dimensional location of medical instrument as claimed in claim 1, characterized in that said fixing pins have the shape of a cylinder, a tapered cylinder, or a rectangle, and the origin enlightening function of said pins is carried out by using a hall sensor or an absolute-angle measuring encoder used in an industrial robot.

13. An apparatus for measuring and fixing the three-dimensional location of medical instrument as claimed in claim 1, wherein said external apparatus includes a general apparatus, selected from a group consisting of a table and an x-ray apparatus, and the installing location is the location where said general apparatus can be assembled to the end-section of said link device.

* * * * *